US008722915B2

(12) United States Patent
Dash et al.

(10) Patent No.: US 8,722,915 B2
(45) Date of Patent: May 13, 2014

(54) PREPARATION OF ORGANOHALOSILANES

(75) Inventors: Aswini K. Dash, Midland, MI (US);
Charles Alan Hall, Crestwood, KY (US); Dimitris Katsoulis, Midland, MI (US); Robert Thomas Larsen, Midland, MI (US); Matthew J. McLaughlin, Midland, MI (US); Jonathan David Wineland, Bedford, KY (US)

(73) Assignee: Dow Corning Corporation, Midland, MI (US)

(*) Notice: Subject to any disclaimer, the term of this patent is extended or adjusted under 35 U.S.C. 154(b) by 0 days.

(21) Appl. No.: 13/637,446

(22) PCT Filed: Apr. 6, 2011

(86) PCT No.: PCT/US2011/031356
§ 371 (c)(1),
(2), (4) Date: Sep. 26, 2012

(87) PCT Pub. No.: WO2011/149593
PCT Pub. Date: Dec. 1, 2011

(65) Prior Publication Data
US 2013/0060060 A1    Mar. 7, 2013

Related U.S. Application Data

(60) Provisional application No. 61/349,245, filed on May 28, 2010.

(51) Int. Cl.
*C07F 7/18*    (2006.01)

(52) U.S. Cl.
USPC ........................................ 556/478; 556/473

(58) Field of Classification Search
CPC ..................................... C07F 7/16; C07F 7/14
USPC ................... 556/450, 472, 478, 473
See application file for complete search history.

(56) References Cited

U.S. PATENT DOCUMENTS

| | | | |
|---|---|---|---|
| 2,403,370 A | 7/1946 | Hurd | |
| 2,888,476 A | 5/1959 | Little et al. | |
| 3,057,686 A | 10/1962 | Muetterties | |
| 4,314,908 A * | 2/1982 | Downing et al. | 502/244 |
| 4,526,769 A | 7/1985 | Ingle et al. | |
| 4,602,101 A * | 7/1986 | Halm et al. | 556/472 |
| 4,836,997 A | 6/1989 | Lepage et al. | |
| 4,864,044 A * | 9/1989 | Lewis et al. | 556/472 |
| 4,888,435 A | 12/1989 | Chadwick et al. | |
| 4,946,980 A | 8/1990 | Halm et al. | |
| 4,973,725 A * | 11/1990 | Lewis et al. | 556/472 |
| 6,156,380 A | 12/2000 | Aramata et al. | |
| 6,326,452 B1 * | 12/2001 | Berrier et al. | 528/12 |
| 6,576,588 B2 * | 6/2003 | Ryu et al. | 502/331 |
| 6,790,749 B2 | 9/2004 | Takemura et al. | |
| 6,887,448 B2 | 5/2005 | Block et al. | |
| 7,223,879 B2 | 5/2007 | Buchwald et al. | |
| 7,442,824 B2 | 10/2008 | Paetzold et al. | |
| 7,559,969 B2 | 7/2009 | Sanjurjo et al. | |
| 7,716,590 B1 | 5/2010 | Nathan | |
| 8,124,809 B2 | 2/2012 | Masaoka et al. | |
| 2005/0074387 A1 | 4/2005 | Bulan et al. | |
| 2005/0220514 A1 | 10/2005 | Hisakuni | |
| 2006/0165580 A1 * | 7/2006 | Lipshutz | 423/314 |
| 2010/0280295 A1 | 11/2010 | Armbruester et al. | |

FOREIGN PATENT DOCUMENTS

| | | |
|---|---|---|
| CA | 2829701 A1 | 9/2012 |
| DE | 3024319 | 1/1982 |
| DE | 4041644 A1 | 6/1992 |
| DE | 19654154 | 6/1997 |
| JP | 51-23226 | 2/1976 |
| JP | 2009111202 | 5/2009 |
| WO | 0248034 | 6/2002 |
| WO | 2005051963 | 6/2005 |
| WO | 2009037301 | 3/2009 |

OTHER PUBLICATIONS

Eaborn, C. et al., Further studies on reactions of organic halides with disilanes catalysed by transition metal complexes, Journal of Organometallic Chemistry, vol. 225, 1982, pp. 331-341.
Golubtsov, S.A. et al., Role of the Products of Partial Chlorination of Silicon in the Formation of Methyltrichlorosilane, Russian Chemical Bulletin, vol. 21, No. 3 (1972), pp. 584-586.
H. Walter, Mechanism of the silicide-catalysed hydrodehalogenation of silicon tetrachloride to trichlorosilane, J. Chem. Soc., Faraday Trans., 1996,92, 4605-4608.
Juszczyk et al., of Pd/SiO2 catalysts during high temperature reduction., Department of Catalysis on Metals, Institute of Physical Chemistry, Polish Academy of Sciences, Warsaw, Pol. Catalysis Letters (2002), 78(1-4), 95-98.
Juszczyk et al., Transformation of Pd/SiO2 into palladium silicide during reduction at 450° and 500° C., Institute of Physical Chemistry, Department of Catalysis on Metals, Polish Academy of Sciences, Warsaw, Pol. Journal of Catalysis (2003), 220(2), 299-308.
Lobusevich, N.P. et al., Reactions During Direct Synthesis of Alkylchlorosilanes., vol. 48, No. 11, 1978, pp. 2534-2541.

(Continued)

*Primary Examiner* — Sudhakar Katakam
*Assistant Examiner* — Pancham Bakshi
(74) *Attorney, Agent, or Firm* — Catherine U. Brown

(57) ABSTRACT

A process for preparing organohalosilanes comprising combining hydrogen, a halosilane having the formula $H_aSiX_{4-a}$ (I) and an organohalide having the formula RX (II), wherein R is $C_1$-$C_{10}$ alkyl or $C_4$-$C_{10}$ cycloalkyl, each X is independently halo, and the subscript a is 0, 1, or 2, in the presence of a sufficient amount of a catalyst effective in enabling the replacement of one or more of the halo groups of the halosilane with the R group from the organohalide, at a temperature from 200 to 800° C., to form an organohalosilane and a hydrogen halide, wherein the volumetric ratio of hydrogen to halosilane is from 1:3 to 1:0.001 and the volumetric ratio of hydrogen to organohalide is from 1:1 to 1:0.001, and wherein the catalyst is optionally treated with the hydrogen or the halosilane prior to the combining.

14 Claims, No Drawings

(56) References Cited

OTHER PUBLICATIONS

Moreno-Manas, Marcial et al., Formation of Carbon—Carbon Bonds under Catalysis by Transition-Metal Nanoparticles, Department of Chemistry, Universitat Autonoma de Barcelona, Barcelona, Spain. Accounts of Chemical Research (2003), 36(8), 638-643.

Dallas T. Hurd, The Vapor Phase Alkylation and Hydrogenation of Chlorosilanes, J. Am. Chem. Soc., 1945, 67 (9), pp. 1545-1548.

Beccalli, Egle M., et al., C—C, C—O, C—N Bond Formation on sp2 Carbon by Palladium(II)-Catalyzed Reactions Involving Oxidant Agents., Istituto di Chimica Organica A. Marchesini, Facolta di Farmacia, Universita di Milano, Milan, Italy. Chemical Reviews (Washington, DC, United States) (2007), 107(11), 5318-5365.

Methivier, et al., Pd/SiC catalysts. Characterization and catalytic activity for the methane total oxidation.. Institut de Recherches sur la Catalyse—CNRS, conventionne a l'Universite Claude Bernard Lyon 1, Villeurbanne, Fr. Journal of Catalysis (1998), 173(2), 374-382.

Srebowata, A. et al., Hydrodechlorination of 1,2-dichloroethane over differently reduced Pd/SiO2 catalysts., Institute of Physical Chemistry, Polish Academy of Sciences, Warsaw, Pol. Polish Journal of Chemistry (2003), 77(12), 1841-1848.

Tanaka, Miyoko et al., Nanomaterials Laboratory, National Institute for Materials Science, Tsukuba, Sakura, Japan. Journal of Crystal Growth (2002), 237-239(Pt. 1), 254-258.

Terao, Jun et al., Transition metal-catalyzed C—C bond formation reactions using alkyl halides., Department of Applied Chemistry and Center for Atomic and Molecular Technologies, Graduate School of Engineering, Osaka University, 2-1 Yamadaoka, Suita, Osaka, Japan. Bulletin of the Chemical Society of Japan (2006), 79(5), 663-672.

Vijh, A. K. et al., Discovery of some new stable electrocatalytic materials for the anodic oxidation of hydrazine., Inst. Rech. Hydro-Quebec, Varennes, QC, Can. Journal of Materials Science Letters (1993), 12(2), 113-15.

Vijh, A. K. et al., Electrochemical activity of silicides of some transition metals for the hydrogen evolution reaction in acidic solutions., International Journal of Hydrogen Energy (1990), 15(11), 789-94.

Yin, Lunxiang, et al., Carbon—carbon coupling reactions catalyzed by heterogeneous palladium catalysts., Institute fuer Chemie, Humboldt-Universitaet Berlin, Berlin, Germany. Chemical Reviews (Washington, DC, United States) (2007), 107(1), 133-173.

\* cited by examiner

PREPARATION OF ORGANOHALOSILANES

CROSS-REFERENCE TO RELATED APPLICATIONS

This application is a U.S. national stage filing under 35 U.S.C. §371 of PCT Application No. PCT/US11/31356 filed on Apr. 06, 2011, currently pending, which claims the benefit of U.S. Provisional Patent Application No. 61/349245, filed May 28, 2010 under 35 U.S.C. §119 (e). PCT Application No. PCT/US11/31356, and U.S. Provisional Patent Application No. 61/349245 are hereby incorporated by reference.

FIELD OF THE INVENTION

The present invention relates to a process for preparing organohalosilanes comprising combining hydrogen, a halosilane and an organohalide in the presence of a catalyst to form an organohalosilane and a hydrogen halide.

BACKGROUND OF THE INVENTION

Organohalosilanes are hydrolyzed to produce a wide range of polyorganosiloxanes, which are sold into many different industries. Typically, organohalosilanes are produced commercially by the Mueller-Rochow Direct Process, which comprises passing an organohalide over zero-valent silicon in the presence of a copper catalyst and various optional promoters to produce a mixture of organohalosilanes.

A typical commercial process to make zero-valent silicon comprises the carbothermic reduction of $SiO_2$ in an electric arc furnace at extremely high temperatures. Generation of these extreme temperatures requires significant amounts of energy, which adds significant cost to the process of producing zero-valent silicon. Consequently, the use of zero-valent silicon also adds significant costs to the production of organohalosilanes.

In addition to by the Direct Process, organohalosilanes have been produced by the alkylation of tetrachlorosilane and various methylchlorosilanes by passing the vapors of these chlorosilanes together with an alkyl halide over finely divided aluminum or zinc at elevated temperatures. However, this process results in the production of a large amount of aluminum chloride or zinc chloride, which is costly to dispose of on a commercial scale.

Therefore, there is a need for a more economical process of producing organohalosilanes that avoids the need for zero-valent silicon and that does not require the costly disposal of byproducts.

BRIEF SUMMARY OF THE INVENTION

The present invention is directed to a process for preparing organohalosilanes comprising combining hydrogen, a halosilane having the formula $H_aSiX_{4-a}$ (I), and an organohalide having the formula RX (II), wherein R is $C_1$-$C_{10}$ alkyl or $C_4$-$C_{10}$ cycloalkyl, each X is independently halo, and the subscript a is 0, 1, or 2, in the presence of a sufficient amount of a catalyst effective in enabling the replacement of one or more of the halo groups of the halosilane with the R group from the organohalide, at temperature from 200 to 800° C., to form an organohalosilane and a hydrogen halide, wherein the volumetric ratio of hydrogen to halosilane is from 1:3 to 1:0.001 and the volumetric ratio of hydrogen to organohalide is from 1:1 to 1:0.001, and wherein the catalyst is optionally treated with the hydrogen or the halosilane prior to the combining.

The process of the present invention produces organohalosilanes from halosilanes. Since halosilanes can be produced using less energy than required to produce zero-valent silicon, the process of the invention may produce organohalosilanes more economically than current processes using zero-valent silicon. Further, the process does not produce large amounts metal halide byproducts requiring costly disposal.

The process of the present invention produces organohalosilanes, which can be hydrolyzed in known processes to produce polyorganosiloxanes. The polyorganosiloxanes thus produced find use in many industries and applications.

DETAILED DESCRIPTION OF THE INVENTION

A process for preparing organohalosilanes, the process comprising:

combining hydrogen, a halosilane having the formula $H_aSiX_{4-a}$ (I), and an organohalide having the formula RX (II), wherein R is $C_1$-$C_{10}$ alkyl or $C_4$-$C_{10}$ cycloalkyl, each X is independently halo, and the subscript a is 0, 1, or 2, in the presence of a sufficient amount of a catalyst effective in enabling the replacement of one or more of the halo groups of the halosilane with the R group from the organohalide, at a temperature from 200 to 800° C., to form an organohalosilane and a hydrogen halide, wherein the volumetric ratio of hydrogen to halosilane is from 1:3 to 1:0.001 and the volumetric ratio of hydrogen to organohalide is from 1:1 to 1:0.001, and wherein the catalyst is optionally treated with the hydrogen or the halosilane prior to the combining.

The hydrogen combined with the halosilane and organohalide is hydrogen gas, $H_2$. Hydrogen is well known in the art and available commercially.

The halosilane has the formula $H_aSiX_{4-a}$ (I), wherein X is halo and the subscript a is 0, 1, or 2; alternatively 0 or 1; alternatively 0. The halo group X is fluoro, chloro, bromo; or iodo, alternatively chloro, bromo, or iodo, alternatively chloro.

Examples of the halosilanes (I) include, but are not limited to, tetrachlorosilane, trichlorosilane ($HSiCl_3$), dichlorosilane ($H_2SiCl_2$), tetrabromosilane, tribromosilane ($HSiBr_3$), dibromosilane ($H_2SiBr_2$), tetraiodosilane, triiodosilane ($HSiI_3$), diiodosilane ($H_2SiI_2$), tetrafluorosilane, trifluorosilane ($HSiF_3$), difluorosilane ($H_2SiF_2$).

Processes of preparing the halosilanes of the invention are known in the art. Many of these compounds are available commercially.

The organohalide has the formula RX (II), wherein R is $C_1$-$C_{10}$ alkyl or $C_4$-$C_{10}$ cycloalkyl, and X is as defined above for the halosilane and may be the same or different as on the halosilane.

The alkyl groups represented by R in formula (II) typically have from 1 to 10 carbon atoms, alternatively from 1 to 6 carbon atoms, alternatively from 1 to 4 carbon atoms. The cycloalkyl groups represented by R in formula (II) typically have from 4 to 10 carbon atoms; alternatively 6 to 8 carbon atoms. Alkyl groups containing at least three carbon atoms can have a branched or unbranched structure. Examples of alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl. Examples of cycloalkyl groups include, but are not limited to, cyclobutyl, cyclopentyl, cyclohexyl, and methylcyclohexyl.

Examples of the organohalide include, but are not limited to, methyl chloride, methyl bromide, methyl iodide, ethyl chloride, ethyl bromide, ethyl iodide, cyclobutyl chloride, cyclobutyl bromide, cyclohexyl chloride, and cyclohexyl bromide.

Processes of preparing the organohalide of the invention are known in the art; many of these compounds are available commercially.

The catalyst is effective in enabling the replacement of one or more of the halo groups of the halosilane with the R group from the organohalide. As used herein, "a catalyst effective in enabling the replacement of one or more of the halo groups of the halosilane with the R group from the organohalide" means a catalyst that, if present when hydrogen, the halosilane, and the organohalide are combined according to the invention, will result in the formation of an organohalosilane as described below by enabling the transfer of an R group (i.e., the alkyl or cycloalkyl group) from the organohalide to the halosilane and the removal of a halo group from the halosilane. As used herein, "catalyst" and "catalyst effective in enabling the replacement of one or more of the halo groups of the halosilane with the R group from the organohalide" are used interchangeably.

The catalyst is at least one metal, or a compound containing at least one metal, from groups IB or VIIIB of the periodic table of elements, namely iron, ruthenium, osmium, cobalt, rhodium, iridium, nickel, palladium, platinum, copper, or gold; alternatively, the catalyst comprises at least one metal, or a metal compound containing at least one metal, selected from iron, ruthenium, osmium, cobalt, nickel, palladium, platinum, copper, and gold; alternatively, the catalyst is at least two metals, or a compound or compounds containing at least two metals, selected from palladium and copper, palladium and gold, palladium and cobalt, palladium and nickel, copper and nickel, copper and cobalt, copper and gold, and nickel and cobalt.

The catalyst can be supported or unsupported. As used herein, "supported" means that the metal, or compound of the metal, as described above, is dispersed across a support's surface or within a support's pores. Supports include, but are not limited to, oxides of aluminum, titanium, zirconium, and silicon. Supports also include, but are not limited to, activated carbon, carbon nanotubes, fullerenes, and other allotropic forms of carbon.

Supported catalysts of the invention typically comprise, based on the weight of the metal and support, from 0.1 to less than 100% (w/w) of the metal, or a compound of the metal, described above; alternatively from 0.1 to 50% (w/w) of a metal, or compound of the metal, described above; alternatively 0.1 to 25% (w/w) of a metal described above; alternatively 1 to 25% (w/w) of a metal described above.

The catalyst can have a variety of physical forms including, but not limited to, lumps, granules, flakes, and powder.

Examples of unsupported catalysts include, but are not limited to, iron, ruthenium, osmium, cobalt, rhodium, iridium, nickel, palladium, platinum, copper, gold, palladium and copper, palladium and gold, palladium and cobalt, palladium and nickel, copper and nickel, copper and cobalt, copper and gold, nickel and cobalt, and salts of these metals, such as $PdCl_2$ or $PdCl_2$ and $CuCl_2$. Examples of supported metallic catalysts include 10 to 25% (w/w), based on the weight of the metal and support, of the unsupported catalyst described above on an activated carbon support.

The unsupported and supported metallic catalyst can be made by processes known in the art. For example, to make the unsupported catalyst, suitable metals may be purchased and then ground to a desired particle size and mixed with any other metals of the catalyst, or one metal may be reduced on another metal by reduction of a salt of the first metal deposited on another one metal (e.g., $CuCl_2$ may be deposited on Pd black then reduced at 500° C. with hydrogen to form a copper on palladium catalyst).

The supported metallic catalysts may be prepared by making a mixture of any metal salt, or salts, in a solvent, such as water or acid, applying the mixture to a support, and, optionally, reducing the metal salt on the surface of the support. For example, $PdCl_2$ and $CuCl_2$, can be dissolved in hydrochloric acid and mixed with activated carbon. Excess metal salt solution can then be removed, and the activated carbon-metal salt mixture dried. The metal salt can then be reduced on the activated carbon with hydrogen, typically at about 500° C., to give the supported catalyst. One skilled in the art would understand that order of addition, reduction and multistep addition of salts and subsequent reduction can also be carried out to prepare the supported catalyst. Furthermore, the metal salt does not need to be soluble in the solvent. The function of the solvent is to deposit the salt on the support and then be able to be removed by common methods such as evaporation. A method of making the supported metallic catalysts is also described in detail in the examples section below. Some of these catalysts are also available commercially.

In one embodiment, the process of the invention does not comprise reactive metals, such as aluminum or zinc, which form metal halides when, for example, methyl chloride and tetrachlorosilane are combined in their presence.

The reactor can be any reactor suitable for the combining of gases and solids. The reactor configuration can be a packed bed, a stirred bed, a vibrating bed, or a fluidized bed. To facilitate reaction, the reactor should have means to control the temperature of the reaction zone.

The temperature at which the hydrogen, the halosilane, and the organohalide are combined in the presence of the catalysts is typically from 200 to 800° C.; alternatively from 300 to 600° C.; alternatively from 350 to 550° C.

The pressure at which the hydrogen, the halosilane, the organohalide are combined in the presence of the catalysts is typically from 0 to 2000 kilopascals gauge pressure (kPag); alternatively from 100 to 2000 kPag; alternatively from 100 to 1000 kPag; alternatively from 100 to 800 kPag, at a temperature from 200 to 500° C.

The process is typically a continuous process although non-continuous processes are also envisioned. As used herein, a "continuous process" is a process where the hydrogen, the halosilane, and the organohalide continuously enter the reactor containing the catalyst, and the organohalosilane and hydrogen halide, described below, continually leave the reactor. The continuous process is typically conducted until the catalyst activity drops below predetermined limits.

The hydrogen, the halosilane and the organohalide are typically combined in the presence of the catalyst by charging the reactor with the catalyst followed by continuously feeding the hydrogen, the halosilane, and the organohalide to the reactor containing the catalyst. The hydrogen, halosilane, and organohalide are typically fed to the reactor simultaneously; however, other methods of combining, such as by separate pulses, are also envisioned.

The hydrogen, the halosilane, and the organohalide are typically fed to the reactor at a flow rate to provide a sufficient contact time, as described below, in the reactor. As used herein, "flow rate" means the volumetric flow rate (e.g., standard cubic centimeters per minute (sccm)). Flow rate may be controlled using a mass flow controller and a bubbler, containing liquid halosilane or organohalide, through which the hydrogen is bubbled. Flow rate of the hydrogen, the halosilane and the organohalide may alternately be controlled through use of independently controlled flow regulation and measurement devices known in the art. Flow rates are typically varied to control contact time for a particular reactor volume.

As used herein, "contact time" means the residence time (i.e., the time for one reactor volume of gas to pass through a reactor charged with catalyst) of the hydrogen, halosilane, and organohalide in the reactor. A sufficient contact time is typically enough time for the hydrogen, the halosilane, and the organohalide to react to form the organohalosilane, described below. For example, a sufficient contact time is typically from 0.1 to 100 seconds (s); alternatively from 0.1 to 10 s; alternatively from 2 to 10 s, at a temperature from 200 to 800° C. Contact time is typically controlled by varying flow rate.

The volumetric ratio of hydrogen to halosilane combined in the process of the invention is from 1:3 to 1:0.001; alternatively from 1:2 to 1:0.001; alternatively from 1:0.8 to 1:0.004; alternatively from 1:0.4 to 1:0.01, at a temperature from about 25.15° C. and at a pressure of 101.325 kPag. The ratio of hydrogen to halosilane is a volumetric ratio (i.e., v/v) and is calculated for standard temperature and pressure. In a continuous process, for example, the volumetric ratio is the ratio of the volumetric flow rates calculated for standard temperature and pressure.

The volumetric ratio of the hydrogen to the organohalide combined in the process of the invention is from 1:10 to 1:0.001; alternatively from 1:1 to 1:0.01; alternatively from 1:0.8 to 1:0.05; alternatively from 1:0.25 to 1:0.05, at a temperature 25.15° C. and at a pressure of 101.325 kPa. The ratio of hydrogen to organohalide is a volumetric ratio (i.e., v/v) and is calculated at standard temperature and pressure. In a continuous process, for example, the volumetric ratio is the ratio of volumetric flow rates as calculated at standard temperature and pressure.

The catalyst is in a sufficient amount. As used herein, a "sufficient amount" of catalyst is enough catalyst to enable the formation of the organohalosilane, described below, when the hydrogen, the halosilane, and the organohalide are combined in the presence of the catalyst. For example, a sufficient amount of catalyst is at least 0.01 mg catalyst/cm$^3$ of reactor volume; alternatively at least 0.5 mg catalyst/cm$^3$ of reactor volume; alternatively from 1 to 10000 mg catalyst/cm$^3$ of reactor volume.

If the organohalide or halosilane are liquids at or below standard temperature and pressure, the process of producing an organohalosilane may further comprise pre-heating and gasifying the organohalide or halosilane by known methods. Alternatively, the process may further comprise bubbling the hydrogen through the liquid organohalide or halosilane to vaporize the liquids before combining in the presence of the catalyst in the reactor.

The process may further comprise pre-heating the catalyst in an inert atmosphere at a temperature up to 700° C., alternatively up to 600° C., alternatively from 280 to 525° C., prior to the combining according to the invention.

The process may further comprise pre-treating the catalyst with the hydrogen or the halosilane at a temperature up to 700° C., alternatively up to 600° C., alternatively from 280 to 525° C., to remove oxygen prior to combining with the organohalide according to the invention. Pre-treating of the catalyst may be accomplished by feeding the hydrogen or halosilane to the reactor containing the catalyst at the temperature described. Pretreating the catalyst with hydrogen or halosilane also encompasses pre-treating the catalyst with both hydrogen and halosilane together.

The process may further comprise recovering the organohalosilane produced. The organohalosilane may be recovered by, for example, removing gaseous organohalosilane from the reactor followed by condensation. The organohalosilanes produced may be isolated by distillation.

The organohalosilane produced by the process for preparing organohalosilanes described and exemplified above has the formula $R_bH_cSiX_{4-b-c}$, wherein R and X are as defined and exemplified above for the organohalide; the subscript b is 1, 2, or 3, alternatively b is 1 or 2; the subscript c is 0, 1, or 2, alternatively 0 or 1; alternatively 0; and the sum of b+c is 1, 2, or 3.

Examples of organohalosilanes prepared according to the present process include, but are not limited to, dimethyldichlorosilane (i.e., $(CH_3)_2SiCl_2$), dimethyldibromosilane, diethyldichlorosilane, diethyldibromosilane, methyltrichlorosilane (i.e., $CH_3SiCl_3$), methyltribromosilane (i.e., $CH_3SiBr_3$), and methyldichlorosilane ($CH_3(H)SiCl_2$).

The hydrogen halide produced according the present process has the formula HX, where X is as defined above for the halosilane and the organohalide. The hydrogen halide may be separated from the organohalosilane via condensation, distillation, or other means and collected or fed to other chemical processes.

The process of the present invention produces organohalosilanes from halosilanes. Since the process produces halosilanes from non-zero-valent silicon, the process of the invention may produce organohalosilanes more economically than current processes using zero-valent silicon. Further, the process of the present invention does not produce metal halide byproducts requiring costly disposal.

The process of the present invention produces organohalosilanes, which can be hydrolyzed in known processes for producing polyorganosiloxanes. The polyorganosiloxanes thus produced find use in many industries and applications.

EXAMPLES

The following examples are presented to better illustrate the process of the present invention, but are not to be considered as limiting the invention, which is delineated in the appended claims. Unless otherwise noted, all parts and percentages reported in the examples are by weight. The following table describes the abbreviations used in the examples:

TABLE 1

| List of abbreviations used in the examples. | |
|---|---|
| Abbreviation | Word |
| g | gram |
| Me | methyl |
| Et | ethyl |
| Pr | n-propyl |
| wt | weight |
| % | percent |
| mol | mole |
| s | second |
| min | minute |
| hr | hour |
| T or Temp. | Temperature |
| ° C. | degrees Celsius |
| K | degrees Kelvin |
| NA | Not Applicable |
| mL | milliliters |
| μL | microliters |
| psig | pounds per square inch gauge pressure |
| kPag | kilo Pascals guage pressure |
| sccm | standard cubic centimeters per minute |

TABLE 1-continued

List of abbreviations used in the examples.

| Abbreviation | Word |
|---|---|
| $H_2$:MeCl Flow Ratio | Ratio of hydrogen to MeCl volumetric flow rates at standard temperature and pressure. |
| $H_2$:$SiCl_4$ Flow Ratio | Ratio of hydrogen to $SiCl_4$ volumetric flow rates at standard temperature and pressure. |
| Standard temperature and pressure | 298.15K and 101.325 kPag. |

The following is a description of the methods and materials that were used in the examples:

Catalysts were prepared by dissolving the halide of a metal, such as $PdCl_2$ and $CuCl_2$, in concentrated hydrochloric acid. In some cases, additional water was added to the solution to ensure complete dissolution of the metal halide. The solution prepared was added to a weighed amount of activated carbon granules. The mixture was placed under vacuum for 20 minutes. After removing the vacuum, the excess liquid was decanted from the activated carbon granules. Next, the granules were blotted dry and dried in an oven overnight at 150° C. After drying, the granules were weighed and the weight of metal on the granules determined by difference. The granules were then placed into a tubular reactor, and the reactor was purged with hydrogen. Next, the catalyst was reduced at 500° C. under hydrogen flow for 2 hours. The catalyst was then typically activated by exposing the catalyst to $H_2$ and $SiCl_4$ for 1 to 5 hours before introducing methyl chloride and starting the reaction.

The reaction apparatus comprised a 4.8 mm inner diameter quartz glass tube in a flow reactor. The reactor tube was heated using a Lindberg/Blue Minimite 2.54 cm tube furnace. Omega FMA 5500 mass flow controllers were used to control gas flow rates. A stainless steel $SiCl_4$ bubbler was used to introduce $SiCl_4$ into the $H_2$ gas stream. The amount of $SiCl_4$ in the $H_2$ gas stream was adjusted by changing the temperature of the $SiCl_4$ in the bubbler based on calculations using well-known thermodynamic principles. The reactor effluent passed through an actuated 6-way valve from Vici.

The reaction products were analyzed using an Agilent Technologies 7890A gas chromatography-mass spectrometry (GC-MS) having two 30 m SPB-Octyl columns (Supelco, 250 μm inner diameter, 0.25 μm thick separation phase coating) in parallel. The GC was configured with two columns in parallel so that a sample could be injected into each column from the same injection port. One column was connected to a mass spectrometry detector, Agilent 7895C, to identify the components in the sample and the other column connected to a thermal conductivity detector (TCD) to quantify the components. The columns of the GC-MS were heated by an Agilent LTM module. The GC-MS was set up in-line with the materials exiting the reactor tube, and samples taken were immediately tested via the 6-way valve with constant 100 μL loop. This configuration allowed the effects of changing reaction conditions to be determined while continuing the reaction.

The activated carbon and metal halide compounds, such as $PdCl_2$ (99.9+), $CuCl_2.2H_2O$ (99.9+), used to make the catalyst used in the examples were purchased from Sigma Aldrich (St. Louis, Mo.). All metal halides used to make the catalyst comprised greater than 99.9% chemical purity or the highest purity available.

Flow rate ratios were determined using the volumetric flow rates, at standard temperature and pressure, of hydrogen, $SiCl_4$, and methyl chloride.

Example 1

A supported catalyst was prepared according to the method described above. The supported catalyst comprised 17% palladium and 1.18% copper on activated carbon. The catalyst was treated with hydrogen and $SiCl_4$ for 1 hour, at 500° C., at a hydrogen flow rate of 100 sccm, a flow ratio of hydrogen to $SiCl_4$ of 1:2.49, and at atmospheric pressure. After one hour, methyl chloride was introduced into the reaction tube with hydrogen and silicon tetrachloride at the various conditions in the table below. The conditions were changed every 10 minutes, and a sample was taken for GC testing after the 10 minutes at the specific reaction conditions. This example demonstrates how varying the temperature, flow rate ratios, and contact time affects the conversion to $MeSiCl_3$. The conditions and analysis results are listed in the following table.

TABLE 2

Conversion of $SiCl_4$ to $MeSiCl_3$ vs. reaction conditions for 17% Pd and 1.18% Cu on activated carbon catalyst.

| Run No. | Reactor Temp. (° C.) | $H_2$ flow rate (sccm) | MeCl flow rate (sccm) | $SiCl_4$ flow rate (sccm) | $H_2$:MeCl flow ratio | $H_2$:$SiCl_4$ flow ratio | $SiCl_4$ conversion to $CH_3SiCl_3$ | Contact time (s) |
|---|---|---|---|---|---|---|---|---|
| 1 | 500 | 100 | 5 | 42.14 | 1:0.05 | 1:0.42 | 1.50 | 0.58 |
| 2 | 500 | 25 | 5 | 12.04 | 1:0.20 | 1:0.48 | 8.32 | 2.03 |
| 3 | 450 | 25 | 5 | 12.04 | 1:0.20 | 1:0.48 | 11.65 | 2.03 |
| 4 | 400 | 25 | 5 | 12.04 | 1:0.20 | 1:0.48 | 12.90 | 2.03 |
| 5 | 350 | 25 | 5 | 12.04 | 1:0.20 | 1:0.48 | 6.66 | 2.03 |
| 6 | 400 | 10 | 5 | 6.02 | 1:0.50 | 1:0.602 | 17.39 | 4.05 |
| 7 | 400 | 10 | 5 | 1.67 | 1:0.50 | 1:0.167 | 16.14 | 5.11 |
| 8 | 400 | 10 | 5 | 0.70 | 1:0.50 | 1:0.070 | 36.56 | 5.43 |
| 9 | 400 | 10 | 5 | 0.38 | 1:0.50 | 1:0.038 | 36.42 | 5.54 |
| 10 | 400 | 7.5 | 5 | 0.32 | 1:0.667 | 1:0.043 | 24.34 | 6.65 |
| 11 | 400 | 20 | 5 | 0.63 | 1:0.25 | 1:0.032 | 57.14 | 3.32 |
| 12 | 400 | 25 | 5 | 0.76 | 1:0.20 | 1:0.030 | 59.37 | 2.77 |
| 13 | 400 | 30 | 5 | 0.88 | 1:0.167 | 1:0.029 | 62.17 | 2.37 |
| 14 | 400 | 40 | 5 | 1.14 | 1:0.125 | 1:0.029 | 61.61 | 1.85 |
| 15 | 400 | 50 | 5 | 1.39 | 1:0.10 | 1:0.028 | 60.52 | 1.51 |
| 16 | 400 | 75 | 5 | 2.02 | 1:0.067 | 1:0.027 | 53.16 | 1.04 |

Examples 2-40

Hydrogen, methyl chloride and silicon tetrachloride were combined in the presence of various unsupported and supported metallic catalysts, prepared according the procedure described above, at different temperatures, gas flow ratios, and contact times. Activated carbon was the support used in examples 2-10, 12-25, 27, 29, and 31-40. Example 11, 26, 28, and 30 did not contain a catalyst support. The results, reaction conditions, gas flow ratios, and catalyst description are listed in following table.

TABLE 3

Summary of exemplary catalysts, reaction conditions and conversion of $SiCl_4$ to $MeSiCl_3$.

| Example No. | Metal/% on activated carbon | Temp. (° C.) | Flow Rate Ratio $H_2$:MeCl | Flow Rate Ratio $H_2$:$SiCl_4$ | Contact Time (s) | Conversion to $MeSiCl_3$ |
|---|---|---|---|---|---|---|
| 2 | Ni/21 | 500 | 1:0.20 | 1:0.036 | 2.76 | 11.76 |
| 3 | Pd/22.6 | 300 | 1:0.42 | 1:0.193 | 13.17 | 14.4 |
| 4 | Cu/17 | 450 | 1:0.20 | 1:0.510 | 1.99 | 2.03 |
| 5 | Pt/12 | 400 | 1:0.05 | 1:0.109 | 0.74 | 1.72 |
| 6 | Co/24.5 | 550 | 1:0.05 | 1:0.004 | 0.81 | 11.8 |
| 7 | Ru/6 | 400 | 1:0.05 | 1:0.044 | 0.78 | 1.84 |
| 8 | Fe/20.0 | 550 | 1:0.05 | 1:0.117 | 0.73 | 2.31 |
| 9 | Au/16.9 | 550 | 1:0.05 | 1:0.117 | 0.73 | 8.03 |
| 10 | OS/1.5 | 550 | 1:0.20 | 1:0.134 | 2.56 | 2.64 |
| 11 | Pd Black* (Sigma) | 400 | 1:0.20 | 1:0.134 | 2.56 | 6.84 |
| 12 | Pd/13.2 Co/1.14 | 375 | 1:0.02 | 1:0.026 | 3.26 | 23.75 |
| 13 | Ni/10.4 Pd/1.84 | 400 | 1:0.25 | 1:0.038 | 3.31 | 19.22 |
| 14 | Pd/16.5 Au/2.65 | 400 | 1:0.25 | 1:0.183 | 2.97 | 22.39 |
| 15 | Pd/17.0 Cu/1.18 | 400 | 1:0.167 | 1:0.029 | 2.37 | 62.17 |
| 16 | Cu/9.6 Fe/7.6 | 550 | 1:0.25 | 1:0.032 | 3.32 | 3.16 |
| 17 | Pd/7.7 Cu/5.8 | 400 | 1:0.167 | 1:0.029 | 2.37 | 16.79 |
| 18 | Pd/18.6 Fe/0.94 | 350 | 1:0.833 | 1:0.047 | 7.55 | 7.92 |
| 19 | Pd/18.8 Cu/0.14 Sn/0.06 | 400 | 1:0.125 | 1:0.028 | 1.85 | 12.76 |
| 20 | Ni/12.2 Cu/0.24 | 500 | 1:0.05 | 1:0.026 | 0.79 | 19.63 |
| 21 | Ni/8.2 Co/5.0 | 500 | 1:1 | 1:0.050 | 0.42 | 19.49 |
| 22 | Co/12.3 Cu/0.76 | 550 | 1:0.20 | 1:0.030 | 2.77 | 11.46 |
| 23 | Au/20.1 Cu/1.86 | 600 | 1:0.05 | 1:0.026 | 0.79 | 11.42 |
| 24 | Pd/18.8 Cu/2.0 | 400 | 1:1 | 1:0.050 | 0.42 | 39.54 |
| 25 | Pd/16.9 Cu/0.90 Zn/0.14 | 400 | 1:1 | 1:0.050 | 0.42 | 53.93 |
| 26 | Cu/0.53 on Pd black* | 550 | 1:.0.20 | 1:0.481 | 2.03 | 3.98 |
| 27 | Pd/17.3 Au/2.69 Cu/1.23 | 400 | 1:1 | 1:0.050 | 0.42 | 44.9 |
| 28 | Cu/0.019 on Pd black* | 550 | 1:0.833 | 1:0.735 | 5.53 | 12.76 |
| 29 | Cu/0.19 Ni/26.7 | 550 | 1:0.05 | 1:0.026 | 0.79 | 8.27 |
| 30 | Cu/0.21 Mg/0.0025 on Pd Black* | 550 | 1:0.20 | 1:0.481 | 2.03 | 3.35 |
| 31 | Cu/0.42 Pd/17.0 Cu1.18 | 550 | 1:0.10 | 1:0.028 | 0.76 | 13.16 |
| 32 | Cu/0.46 Pt/10 | 480 | 1:1 | 1:0.050 | 1.66 | 6.01 |
| 33 | Cu/8.80 Pd0.98 | 600 | 1:0.05 | 1:0.026 | 0.79 | 18.91 |
| 34 | Cu/8.80 Pd/0.98 | 500 | 1:0.05 | 1:0.026 | 0.79 | 16.24 |
| 35 | Pd/13.2 Cu/0.92 | 400 | 1:0.167 | 1:0.029 | 2.37 | 29.73 |
| 36 | Pd/1.70 Cu/0.12 | 400 | 1:0.167 | 1:0.029 | 2.37 | 20.32 |
| 37 | Pd/18.6 Cu/1.34 Al/0.30 | 400 | 1:0.167 | 1:0.029 | 2.37 | 29.27 |
| 38 | Pd/18.6 Cu/0.96 P/0.71 | 400 | 1:0.167 | 1:0.029 | 2.37 | 35.2 |
| 39 | Pd/14.0 Cu/0.98 Au/0.68 | 400 | 1:0.167 | 1:0.029 | 2.37 | 33.52 |
| 40 | Rh/7.3 | 400 | 1:0.20 | 1:0.481 | 2.03 | 0.68 |

*No activated carbon present.

Example 41

A 0.53% Cu on Pd black unsupported bimetallic catalyst was prepared by dissolving 0.0123 g $CuCl_2 \cdot 2H_2O$ in 10 mL de-ionized water. This solution (1.03 mL) was added to 0.1077 g of high surface area Pd black (Sigma-Aldrich). After pulling vacuum for 20 minutes to infuse the solution into the pores of the Pd black and allowing the particles to settle, 0.56 mL of solution was removed leaving 0.47 mL of $CuCl_2 \cdot 2H_2O$ solution mixed with Pd black. The solution was vacuum dried at 50° C. for 2 hours. The catalyst as prepared contained 0.20% Cu metal content by weight on Pd black. Next, the catalyst was placed immediately in a tubular reactor, and then purged with $H_2$ and reduced at 500° C. under 100 sccm flow of hydrogen for 2 hours. The catalyst was then exposed to $H_2$ and $SiCl_4$ for 1 hour at 550° C. The reaction was then begun by introducing $H_2$, $SiCl_4$, and MeCl into the reactor. Samples were taken and tested as described above. At 550° C., 0 psig, a flow rate ratio of $H_2$ to MeCl of 1:0.05, a flow rate ratio of $H_2$ to $SiCl_4$ of 1:0.42, and a contact time of approximately 0.4 seconds, the reaction yielded approximately 4% of $Me_2SiCl_2$, based upon the $SiCl_4$ flow, and 2.14% of $MeSiCl_3$, on the same basis.

Example 42

In a flow reactor, approximately 0.5 g of 13.2% Pd and 0.92% Cu on activated carbon catalyst, prepared as described above, were loaded into the reactor tube as described above. The catalyst was activated by flowing hydrogen and $SiCl_4$ through the catalyst for an hour at 500° C., and then the reaction was started by flowing $H_2$, $SiCl_4$ and 1-chloropropane into the reactor. The 1-chloropropane and $SiCl_4$ were added to the hydrogen flow by bubbling hydrogen through a bubbler containing liquid 1-chloropropane and $SiCl_4$. Samples were taken from the reactor and analyzed by GC-MS as described above. The reaction was run while varying the reaction temperature, flow rate of hydrogen, and $SiCl_4$/1-chloropropane bubbler temperature. The catalyst activation and reaction were done at atmospheric pressure. This example demonstrates that the process of the invention can be used to make propyltrichlorosilane from tetrachlorosilane. The results at the various conditions tested are listed in the following table.

TABLE 4

Conversion of SiCl$_4$ to n-PrSiCl$_3$ vs. reaction conditions for 13.2% Pd and 0.92% Cu on activated carbon catalyst.

| Run No. | H$_2$ flow (sccm) | SiCl$_4$/ PrCl bubbler temp (° C.) | Reactor temp (° C.) | Flow Rate Ratio H$_2$:PrCl | Flow Rate Ratio H$_2$:SiCl$_4$ | Contact Time (s) | Conversion to PrSiCl$_3$ (%) |
|---|---|---|---|---|---|---|---|
| 1 | 30 | 25 | 500 | 1:0.344 | 1:0.157 | 1.89 | 1.25 |
| 2 | 30 | 25 | 400 | 1:0.344 | 1:0.157 | 1.89 | 0.42 |
| 3 | 30 | 25 | 300 | 1:0.344 | 1:0.157 | 1.89 | 0.09 |
| 4 | 30 | 0  | 500 | 1:0.093 | 1:0.046 | 2.49 | 2.87 |
| 5 | 10 | −10 | 500 | 1:0.053 | 1:0.026 | 7.90 | 1.02 |
| 6 | 30 | −10 | 500 | 1:0.053 | 1:0.026 | 2.63 | 3.30 |
| 7 | 30 | −25 | 500 | 1:0.022 | 1:0.011 | 2.75 | 4.71 |
| 8 | 30 | 25 | 600 | 1:0.022 | 1:0.011 | 2.75 | 1.62 |

Example 43

In a flow reactor, approximately 0.5 g of a supported catalyst comprising 18.8 wt % Pd and 2.0 wt % Cu on activated carbon, prepared as described above, were loaded into the reactor tube as described above. The catalyst was activated, and then the reaction was started by flowing H$_2$, SiCl$_4$ and chloroethane into the reactor at the appropriate conditions. Samples were taken and analyzed by GC-MS as described above. The reaction was run while varying the reaction temperature, flow rate of hydrogen, flow rate of chloroethane, SiCl$_4$ bubbler temperature and pressure. The catalyst activation was done at atmospheric pressure. This example demonstrates that the process of the invention can be used to make ethyltrichlorosilane from tetrachlorosilane and the effects of varying pressure, temperature and flow ratios. The results at the various conditions are listed in the following table.

TABLE 5

Conversion of SiCl$_4$ to EtSiCl$_3$ vs. reaction conditions for 18.8% Pd and 2.0% Cu on activated carbon catalyst.

| Run No. | Reactor T (° C.) | Pressure (psig) | SiCl4 bubbler T (° C.) | Flow Rate Ratio H$_2$:EtCl | Flow Rate Ratio H$_2$:SiCl$_4$ | Conv. to EtSiCl$_3$ (%) |
|---|---|---|---|---|---|---|
| 1  | 300 | 1  | 25  | 1:0.167 | 1:0.527 | 0.02 |
| 2  | 400 | 1  | 25  | 1:0.167 | 1:0.527 | 0.60 |
| 3  | 500 | 1  | 25  | 1:0.167 | 1:0.527 | 1.55 |
| 4  | 600 | 1  | 25  | 1:0.167 | 1:0.527 | 1.18 |
| 5  | 500 | 1  | 0   | 1:0.167 | 1:0.130 | 3.19 |
| 6  | 500 | 1  | −10 | 1:0.167 | 1:0.069 | 3.79 |
| 7  | 450 | 1  | 0   | 1:0.167 | 1:0.130 | 2.78 |
| 8  | 400 | 1  | 0   | 1:0.167 | 1:0.130 | 1.75 |
| 9  | 500 | 1  | 25  | 1:0.167 | 1:0.527 | 1.70 |
| 10 | 500 | 10 | 0   | 1:0.1   | 1:0.070 | 3.23 |
| 11 | 500 | 3  | −10 | 1:0.167 | 1:0.060 | 2.70 |
| 12 | 500 | 10 | −10 | 1:0.1   | 1:0.040 | 1.21 |
| 13 | 500 | 8  | −10 | 1:0.083 | 1:0.043 | 1.11 |
| 14 | 500 | 8  | −10 | 1:0.083 | 1:0.043 | 0.93 |
| 15 | 500 | 10 | −10 | 1:0.083 | 1:0.040 | 0.85 |
| 16 | 500 | 10 | −10 | 1:0.125 | 1:0.041 | 1.04 |

That which is claimed is:

1. A process for preparing organohalosilanes, the process comprising:
combining hydrogen, a halosilane having the formula H$_a$SiX$_{4-a}$ (I), and an organohalide having the formula RX (II), wherein R is C$_1$-C$_{10}$ alkyl or C$_4$-C$_{10}$ cycloalkyl, each X is independently halo, and the subscript a is 0, 1, or 2, in the presence of a sufficient amount of a catalyst effective in enabling the replacement of one or more of the halo groups of the halosilane with the R group from the organohalide, at a temperature from 200 to 800° C., to form an organohalosilane and a hydrogen halide, wherein the catalyst is at least one metal selected from iron, ruthenium, osmium, cobalt, nickel, palladium, platinum, copper, and gold wherein the volumetric ratio of hydrogen to halosilane is from 1:3 to 1:0.001 and the volumetric ratio of hydrogen to organohalide is from 1:10 to 1:0.001, and wherein the catalyst is optionally treated with the hydrogen or the halosilane prior to the combining.

2. The process of claim 1, wherein the organohalosilane has the formula R$_b$H$_c$SiX$_{4-b-c}$, wherein the subscript b is 1, 2, or 3, the subscript c is 0, 1, or 2, and b+c is 0, 1, 2, or 3.

3. The process of claim 2, wherein the subscript b is 1 or 2 and the subscript c is 0.

4. The process of claim 1, wherein R is methyl, X is chloro, and a is 0.

5. The process of claim 1, further comprising recovering the organohalosilane.

6. The process of claim 1, wherein the temperature is from 350 to 550° C.

7. The process of 1, wherein the catalyst is a supported catalyst and wherein the support is activated carbon.

8. The process of claim 1, wherein the catalyst effective in enabling the exchange of the R groups of the organohalide with the halo groups of the halosilane is at least two metals selected from palladium and copper, palladium and gold, palladium and cobalt, palladium and nickel, copper and nickel, copper and cobalt, copper and gold, and nickel and cobalt.

9. The process of claim 8 wherein the catalyst is a supported catalyst and wherein the support is activated carbon.

10. The process of claim 1 wherein the ratio of hydrogen to halosilane is from 1:0.8 to 1:0.004 and the ratio of hydrogen to organohalide is from 1:1 to 1:0.01.

11. The process of claim 1, wherein the process is a continuous process and wherein the hydrogen, the halosilane, and organohalide have a contact time between 0.1 and 100 seconds.

12. The process of claim 1, wherein the R is methyl, X is chloro, a is 0, the catalyst is copper deposited on palladium black, and the organohalosilane has the formula R$_b$H$_c$SiX$_{4-b-c}$, herein the subscript b is 2, and the subscript c is 0.

13. The process of claim 1, wherein R is methyl, X is chloro, a is 0, the catalyst is pallaldium and copper, the catalyst is on an activated carbon support, and the organohalosilane has the formula R$_b$H$_c$SiX$_{4-b-c}$, wherein the subscript b is 1, and the subscript c is 0.

14. The process of claim 1, further comprising hydrolyzing the organohalosilane to produce a polyorganosiloxane.

* * * * *